US008142995B2

(12) United States Patent
Hirowatari et al.

(10) Patent No.: US 8,142,995 B2
(45) Date of Patent: Mar. 27, 2012

(54) METHOD FOR ASSESSING ARTERIOSCLEROSIS AND DIABETIC NEPHROPATHY

(75) Inventors: Yuji Hirowatari, Kanagawa (JP); Katsuko Hara, Nara (JP); Hakuo Takahashi, Shiga (JP)

(73) Assignees: Tosoh Corporation, Yamaguchi-ken (JP); Kansai Medical University, Osaka (JP)

( * ) Notice: Subject to any disclaimer, the term of this patent is extended or adjusted under 35 U.S.C. 154(b) by 0 days.

(21) Appl. No.: 12/046,106

(22) Filed: Mar. 11, 2008

(65) Prior Publication Data

US 2008/0160562 A1    Jul. 3, 2008

Related U.S. Application Data

(62) Division of application No. 11/367,454, filed on Mar. 6, 2006, now abandoned.

(30) Foreign Application Priority Data

Mar. 7, 2005    (JP) ................................ 2005-062799

(51) Int. Cl.
  *C12Q 1/00*    (2006.01)
(52) U.S. Cl. ................................. 435/4; 435/2
(58) Field of Classification Search ........................ None
  See application file for complete search history.

(56) References Cited

U.S. PATENT DOCUMENTS 6,485,753 B2    11/2002    Hirowatari et al.
2002/0052017 A1    5/2002    Hirowatari et al.

FOREIGN PATENT DOCUMENTS

| JP | 2002-277461 A | 9/2002 |
| JP | 2004-309133 A | 4/2004 |
| WO | WO 2005/012254 A1 | 2/2005 |

OTHER PUBLICATIONS

Doggrell, Sheila A., "The role of 5-HT on the cardiovascular and renal systems and the clinical potential of 5-HT modulation", Expert Opinion Investigative Drugs, 2003, vol. 12, No. 5, pp. 805-823.*
Hara et al., Journal of Laboratory and Clinical Medicine, Jul. 2004, vol. 144, issue 1, pp. 31-37 (text), and 6 pages of figures.
Ma Yszko J et al; "[Blood platelet function, plasma serotonin and lipid metabolism in patents with diabetic nephropathy]"; Polskie Archiwum Medycyny Wewn Trznej. Jul. 1995, vol. 94, No. 1, pp. 26-31 XP008063455.
Malyszko J et al.: "Platelet function, fibrionolysis, serotonin and serum lipids in diabetic nephropathy: A possible link?" Nephrology Dialysis Transplantation, vol. 9, No. 7, 1994, pp. 955-956, XP008063487.
31$^{st}$ Annual Congress of the European Dialysis and Transplant Association-European Renal Association; Vienna, Austria; Jul. 3-6, 1994 ISSN: 0931-0509 p. 955, col. 2, paragraph 3—p. 956, col. 1, paragraph 1.
WEBMD; pp. 1-2, retrieved from the Internet on Jul. 4, 2007.
Allison et al: "Clinicopathlogic Correlations in Coronary Atherosclerosis. Four Hundred Thirty Patients Studied with Postmortem Coronary Angiography." Circulation, vol. 27, Feb. 1963, pp. 170-184, ISSN: 0009-7322.
Database Embase Elsevier Science Publishers, Amsterdam, NL; 1973, Tokarenko A 1: "Role of serotonin and the sympathicoadrenal system in the pathogenesis of hypertensive disease (Russion)".
Database Medline US National Library of Medicine (NLM), Bethesda, MD, US; 1989, Khrapova E V et al.; "Dynamics of blood serotonin contents in acute disorders of cerebral circulation and circulatory encephalopathy".
Database Medline US National Library of Medicine (NLM), Bethesda, MD, US; 1989, Launay J. M. et al.; "Serotonin and human immunodeficiency viruses."
Database Embase Elsevier Science Publishers, Amsterdam, NL, 1996, Lechin F et al: "Increased levels of free serotonin in plasma of symptomatic asthmatic patients".
O'Leary DH et al., N Engl J. Med, 340(1), p. 14-22 (1999).
Zureik M. et al., Arterioscler Thromb Base Biol, 19(2), p. 366-371)(1999).
Murabito, JM et al., Arch Intern Med, 163(16), p. 1939-1942(2003).
Yokota Tsukasa et al., Nihon Rinsho, suppl. Blood/Urine Chemical Examinations Immunological Testing (No. 1), p. 402-407(1989).
Current Medical vol. 43, Japanese Edition, Nikkei BP p. 1218-1219(2004).
Hirowatari Y et al., Clin Biochem, 37, p. 191-197(2004).
Shuttleworth RD. Intraplatelet serotonin and plasma 5-hydroxyindoles in health and disease. Blood (1981) 57 p. 505-509.
Barradas MA. Intraplatelet serotonin in the patients with diabetes mellitus and peripheral vascular disease. Eur J of Clin Invest (1988) 18 p. 399-404.
Mihai K. Serotonin concentration in offspring of patients suffering from premature coronary arterial disease. Acta Paediatrica Hungarica (1992) 32 p. 319-324.
Pietraszek MH. Serotonin as a factor involved in pathophysiology of thromboangiitis obliterans. Int Angiol (1993) 12 p. 9-12.
Cheshire NJW. Smoking and plasma fibrinogen, lipoprotein (a) and serotonin are markers for postoperative infrainguinal graft stenosis. Eur J Vasc Endovase Surg (1996) 11 p. 479-486.
Schins A. Whole blood serotonin and platelet activation in depressed post-myocardial infarction patents. Life Sciences (2004) 76 p. 637-650.

(Continued)

*Primary Examiner* — L Schuberg
(74) *Attorney, Agent, or Firm* — Sughrue Mion, PLLC

(57) ABSTRACT

A method for assessing arteriosclerosis comprising measuring the serotonin level in whole blood, serum or platelet-rich plasma and rating the serotonin level on such a scale that the lower it is, the more serious the arteriosclerosis is.

2 Claims, 2 Drawing Sheets

OTHER PUBLICATIONS

Kerr PG. Whole blood serotonin levels are markedly elevated in patients or dialytic therapy. Am J Nephrol (1992)12 p. 14-18.

Barradas MA. Intraplatelet serotonin, β-thromboglobulin, and histamine concentrations and thromboxane A2 synthesis in renal disease. Am J Clin Pathol (1991) 96 p. 504-511.

Pietraszek MH. Blood serotonergic mechanisms in type 2 (non-insulin-dependent) diabetes mellitus. Thromnbosis research (1992) 66 p. 765-774.

Steyn ME. Whole blood serotonin levels in chronic renal failure. Life Sciences (1992) 51 p. 359-366.

Ishizaki F. A follow-up study of platelet-rich plasma serotonin in clinical subtypes of cerebral infraction. J Neural Transm (1987) 69 p. 123-129.

Ishizaki F. Plasma serotonin contents in cerebrovacular disease. J. Neural Transm (1978) 43 p. 133-141.

Malysko, J.S. et al., "Hemostasis, Platelet Function and Serotonin in Acute and Chronic Renal Failure", Departments of Nephrology and Pharmacodynamics, Bialystok Medical School, Poland; Thrombosis Research, vol. 83, No. 5, pp. 351-361, 1996.

Malysko, J.S. et al., "Platelet Function, Plasma Serotonin and Serum Lipids in Patents With Diabetic Nephropathy," Pol. Arch. Med. WEWN., 1995, 94 pp. 26-31.

Stoilov LD et al., Metabolism of Various Biogenic Amines in Diabetes Mellitus, Probl. Endokrinol, (Mosk), 1981, p. 3-6, 27(6), (Abstract).

Andrzejewska-Buczko J et al., Serotonin in Diabetic Retinopathy, Klin Oczna, Feb. 1996, p. 101-4, 98(2), (Abstract).

F.J. Martin, et al; Effect of Streptozotocin-induced diabetes mellitus on serotonin measures of peripheral tissues in rats; Life Sciences, vol. 56, No. 1, pp. 51-59, 1995.

Japanese Office Action mailed May 25, 2010, pp. 1-7.

* cited by examiner

METHOD FOR ASSESSING ARTERIOSCLEROSIS AND DIABETIC NEPHROPATHY

This is a divisional of application Ser. No. 11/367,454, filed Mar. 6, 2006 which claims the priority of Japanese Appln. No. 2005-062799 filed Mar. 7, 2005, the disclosures of which are hereby totally incorporated by reference.

The present invention relates to methods for assessing arteriosclerosis and diabetic nephropathy, which make it possible to know how serious arteriosclerosis or diabetic nephropathy.

Arteriosclerosis causes various diseases such as myocardial infarction, cerebral infarction, peripheral circulatory disorder, obstructive arteriosclerosis, peripheral neuropathy, visual disorder and nephropathy. Therefore, it is important to know how serious it is. Conventionally, arteriosclerosis has been evaluated by measuring the thickness of the carotid-artery intima and media by ultrasonography (O'Leary D H et al., N Engl J Med, 340(1), p. 14(1999) and Zureik M et al., Arterioscler Thromb Vasc Biol, 19(2), p 366(1999)), by measuring the difference between the arterial wave velocities in upper and lower extremities (pulse wave velocity) (Murabito J M et al., Arch Intern Med, 163(16), p 1939(2003)) or by measuring a digitized arterial pulse wave form (accelerated arterial plethysmograpm). For measurement of pulse wave velocity, sphygmographs such as VaSera VS-1000 manufactured by Fukuda Denshi and Form PWV/ABI manufactured by Colin may be used, and for measurement of plethysmograms, plethysmographs such as Dinapulse SDP-100 manufactured by Fukuda Denshi and BC Checker manufactured by Future Wave may be mentioned.

Nephropathy is a common complication among diabetes patients and, in serious cases, requires lifelong hemodialysis treatment. The need for regular hospital visits for time-consuming hemodialysis treatment interferes with patients' daily life. Therefore, it is important to detect nephropathy early and prevent its progress chemotherapeutically to be in no need of hemodialysis treatment. Nephropathy is conventionally assessed by measuring creatinine (Yokota Tsukasa et al, Nihon Rinsho, suppl. Blood/Urine Chemical Examinations Immunological Testing (No. 1), p 407(1989)) or urinary albumin (Current Medical vol. 43, Japanese Edition, Nikkei BP (2004)). Its earlier diagnosis and exact evaluation are demanded.

The above-mentioned method of evaluating arteriosclerosis has some problems with sensitivity and accuracy and, besides, requires special equipment. Therefore, there is demand for a simple method available with blood samples. Further, a method for early diagnosis of diabetic nephropathy is demanded, as mentioned above.

The present inventors found that patients with coronary disease show higher platelet-poor plasma serotonin levels and lower whole blood serotonin levels than healthy subjects (JP-A-2002-277461). It is considered that in arteriosclerotic lesions, specifically stimulated platelets release serotonin to increase the serotonin level outside platelets (platelet-poor plasma serotonin level), and subsequent consumption of serotonin in the arteriosclerotic lesions leads to decrease in the total blood serotonin level (whole blood serotonin level).

Thus, there is a close association between change in blood serotonin level and progress of arteriosclerosis. Arteriosclerosis is a main possible cause of diabetic nephropathy which occurs when renal capillaries are damaged. Therefore, blood serotonin level is highly promising as an index of nephropathy. Under these circumstances, the present inventors conducted extensive research and have accomplished the present invention.

Namely, the present invention provides a method for assessing arteriosclerosis comprising measuring the serotonin level in whole blood, serum or platelet-rich plasma and rating the serotonin level on such a scale that the lower it is, the more serious the arteriosclerosis is. The present invention also provides a method for assessing diabetic nephropathy comprising measuring the serotonin level in whole blood, serum or platelet-rich plasma and rating the serotonin level on such a scale that the lower it is, the more serious the diabetic nephropathy is. The present invention further provides a method for assessing diabetic nephropathy comprising measuring the serotonin level in platelet-poor plasma and rating the serotonin level on such a scale that the higher it is, the more serious the nephropathy is. The present invention still further provides a method for assessing diabetic nephropathy which comprises a) measuring the whole blood, serum or platelet-rich plasma serotonin level in an individual; b) measuring the platelet-poor plasma serotonin level in the same individual; and c) rating the ratio of the platelet-poor plasma serotonin level obtained in b) to the whole blood, serum or platelet-rich plasma serotonin level obtained in a) on such a scale that the higher the ratio is, the more serious the diabetic nephropathy.

Now, the present invention will be described in detail.

The present invention provides new indices for assessment of arteriosclerosis and diabetic nephropathy. Especially, it makes it possible to assess diabetic nephropathy and know its exact pathologic condition by measuring the serotonin levels both in whole blood, serum or platelet-rich plasma and in platelet-poor plasma. Further, it is also possible to assess diabetic nephropathy and know its exact pathologic condition from the ratio of platelet-poor plasma serotonin level to whole blood, serum or platelet-rich plasma serotonin level.

In the present invention, serum is the supernatant of blood obtained after coagulation and centrifugation. Because serotonin is released from platelets upon blood coagulation, serotonin in serum reflects serotonin in whole blood, i.e., total blood serotonin.

In the present invention, platelet-rich plasma means the supernatant of blood collected with an anticoagulant for inhibition of coagulation obtained after mild centrifugation. The "mild centrifugation" means centrifugation under conditions that allow sedimentation of erythrocytes, but prevent sedimentation of platelets, for example, at 450×g for 5 minutes. Serotonin in platelet-rich plasma reflects serotonin in whole blood, i.e., total blood serotonin.

Further, in the present invention, platelet-poor plasma means the supernatant of blood collected with an anticoagulant for inhibition of coagulation after severe centrifugation. The "severe centrifugation" means centrifugation under conditions that allow all hemocytes including platelets to sediment, for example, at 1,000×g for 30 minutes.

The methods of the present invention require measurement of the serotonin level in whole blood, serum or platelet-rich plasma or the serotonin level in platelet-poor plasma. The measurement may be done by any method without any particular restrictions, for example, by liquid chromatography or immunoassay. For measurement of total blood serotonin by liquid chromatography which is usually preceded by deproteinization of samples, it is common to use whole blood collected in a blood collection tube containing an anticoagulant as a sample. In measurement of total blood serotonin by immunoassay, a serum sample is usually used without deproteinization pretreatment of the sample.

EXAMPLES

The present invention will be described in further detail with reference to Examples. However, the present invention is by no means restricted to such specific Examples.

Example 1

Figure 1:
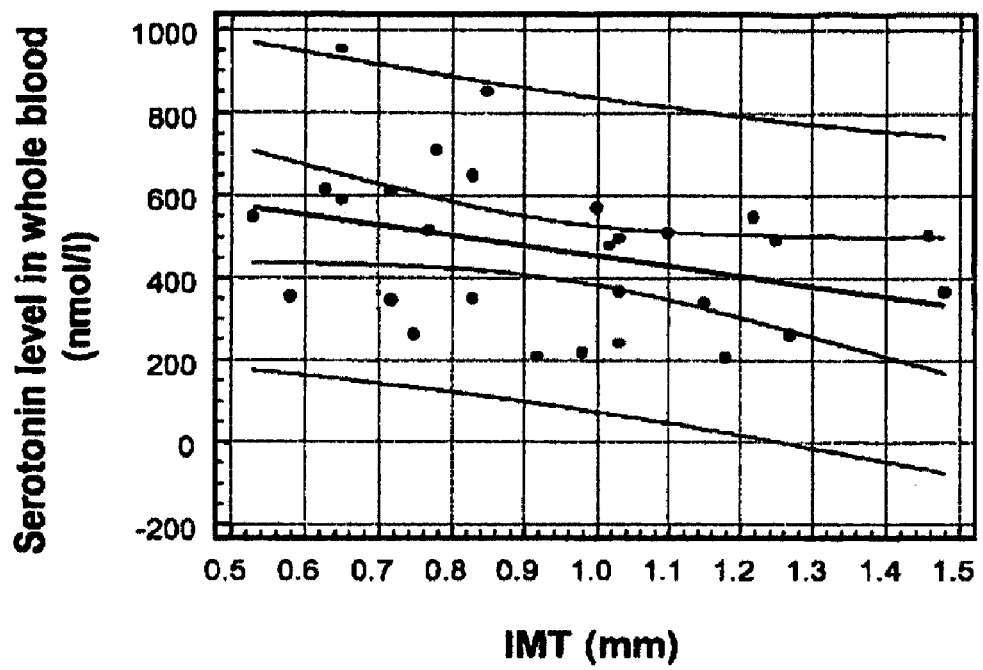
FIG. 1 shows the relationship between the IMT values and the whole blood serotonin levels obtained in Example 1.

Whole blood and platelet-poor plasma serotonin levels were measured in 24 diabetes patients, and the carotid-artery intima and media thicknesses (IMT) were measured by ultrasonography. Patients under hemodialysis treatment had been eliminated preliminarily. The whole blood and platelet-poor plasma serotonin levels were measured in accordance with Hirowatari Y et al., Clin Biochem, 37, p 191(2004). IMT was measured at three sites with the Aloka SSD-1700 and averaged. Creatinine in serum samples was measured with AquaAuto CRE-II reagent, Kainos. IMT was compared with whole serotonin level, platelet-poor plasma serotonin level and the ratio of platelet-poor plasma serotonin level to whole blood serotonin and had a correlation only with blood serotonin level. The results are shown in FIG. 1. The whole blood serotonin level showed significant decrease with increase in IMT (correlation coefficient −0.37, significant difference 0.55). The statistical analyses were performed with Spearman's rank correlation test. The solid lines in FIG. 1 indicate the correlation line, the 95% confidence intervals and the 95% prediction intervals.

The good correlation between whole blood serotonin level and IMT, which reflects the seriousness of arteriosclerosis, suggests that it is possible to a lower whole blood serotonin level as more serious arteriosclerosis.

Example 2

Figure 2:
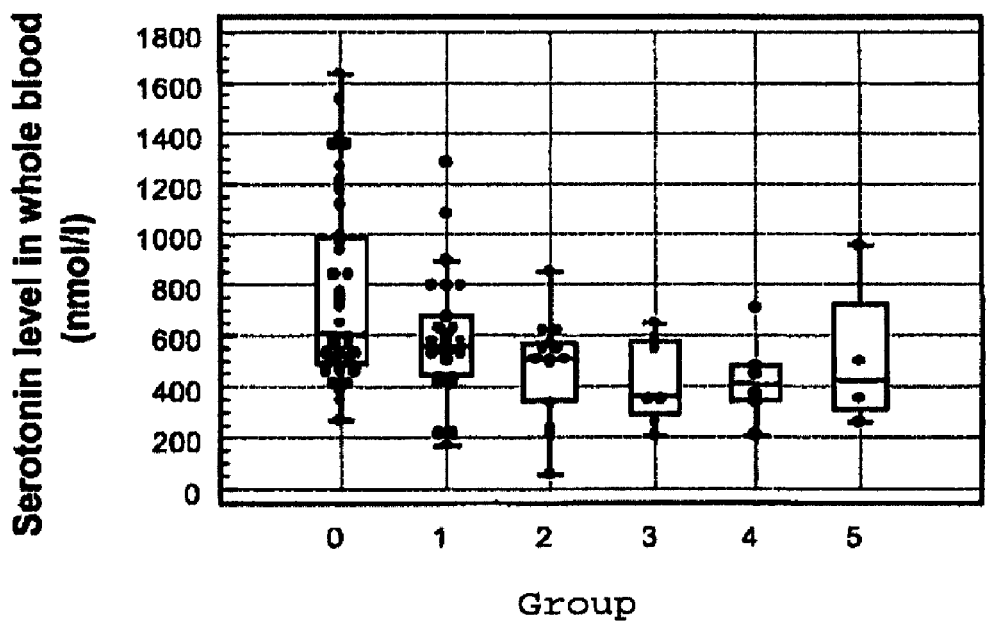
FIG. 2 shows the whole blood serotonin levels in the respective groups obtained in Example 2.

Whole blood and platelet-poor plasma serotonin levels were measured in 38 healthy subjects and 52 diabetes patients. Creatinine was also measured in the diabetes patients. The measurements were done in the same manner as in Example 1. Patients under hemolysis treatment had been eliminated preliminarily. All the subjects were divided into six groups: healthy subjects, diabetes patients with at most 1.2 mg/dl creatinine, diabetes patients with at most 2.0 mg/dl creatinine, diabetes patients with at most 4.0 mg/dl creatinine, diabetes patients with at most 6.0 mg/dl creatinine and diabetes patients with at most 8.0 mg/dl creatinine (designated as groups 0 to 5, respectively), and the ratio of platelet-poor plasma serotonin level to whole blood serotonin level was compared between the groups. The results are shown in FIG. 2. FIG. 2 indicates that whole blood serotonin level tends to be lower in the diabetic patients than in the healthy subjects and that among the diabetic groups, there was a tendency that whole blood serotonin level decreases with increase in creatinine. The ANOVA significant test revealed good significant differences (P=0.003), especially P<0.05 between group 0 (healthy) and group 1 (creatinine at most 1.2 mg/dl) and between group 0 (healthy) and group 2 (creatinine at most 2.0 mg/dl). Diabetes mellitus has a high risk of nephropathy, and an elevated creatinine level indicates progress of diabetic nephropathy. Therefore, a decreased whole blood serotonin level reflects progress of diabetic nephropathy.

Figure 3:
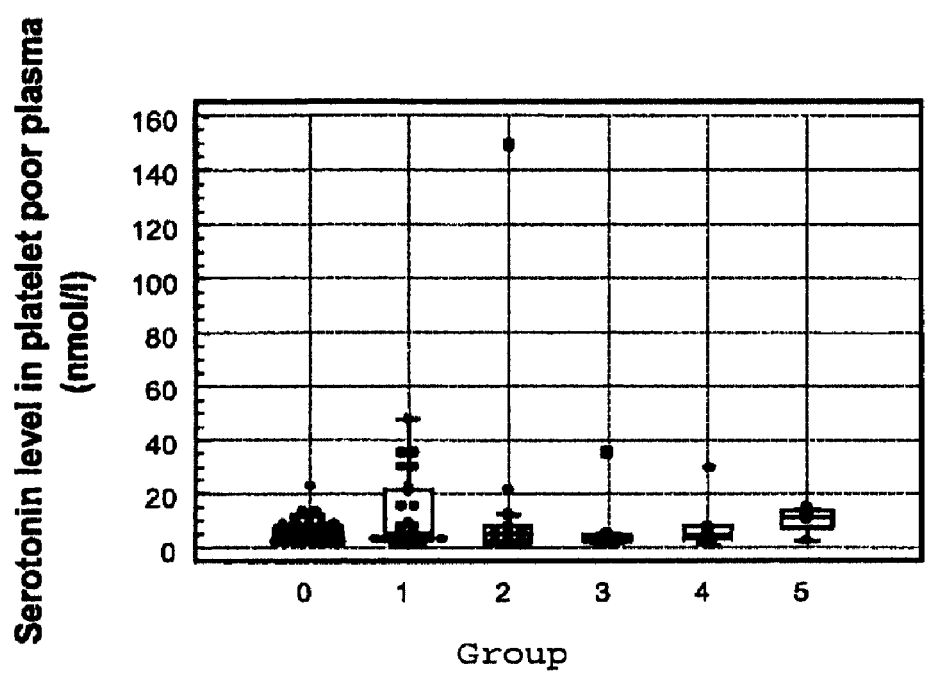
FIG. 3 shows the platelet-poor plasma serotonin levels in the respective groups obtained in Example 2.
Figure 4:
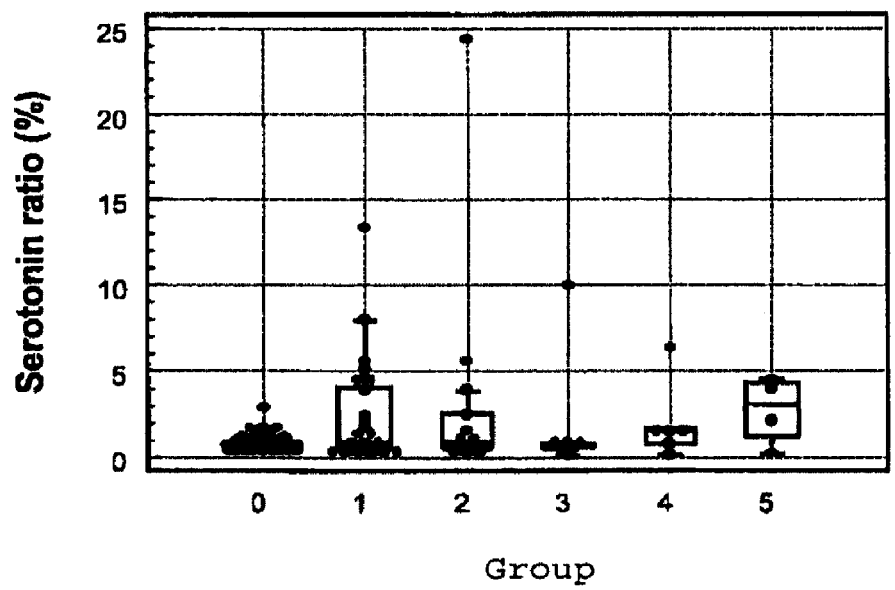
FIG. 4 shows the ratios of platelet-poor plasma serotonin level to whole blood serotonin level in the respective groups obtained in Example 2.

The platelet-poor plasma serotonin level and the ratio of platelet-poor plasma serotonin level to whole blood serotonin level for each group is shown in FIG. 3 and FIG. 4. FIG. 3 and FIG. 4 show that there are some cases in group 1 (creatinine at most 1.2 mg/dl) to group 4 (creatinine at most 6.0 mg/dl) which showed apparently higher values (platelet-poor plasma serotonin level of at least 20 mmol/l and a ratio of platelet-poor plasma serotonin level to whole blood serotonin level of at lease 5%) than healthy subjects (group 1). Most of them were found in group 1 (creatinine level at most 1.2 mg/dl), including 8 patients with a platelet-poor plasma serotonin level of 20 mmol/l or above and 4 patients with a ratio of platelet-poor plasma serotonin to whole blood serotonin of 5% or above. On the other hand, group 5 included no patients with a platelet-poor plasma serotonin level of 20 mmol/l or above and a ratio of platelet-poor plasma serotonin to whole blood serotonin of 5% or above. This suggests that platelet-poor plasma serotonin level and the ratio of platelet-poor plasma serotonin level to whole blood serotonin level elevate at the initial phase of diabetic nephropathy and then return to normal as nephropathy progresses.

Whole blood serotonin level was considerably lower in group 5 than in healthy subjects. It is considered that intense local vascular inflammations occur at the initial phase of diabetic nephropathy with activation of platelets at the inflamed regions results and resultant increase in platelet-poor plasma serotonin level, and at the later phases of diabetic nephropathy (the chronic phase of arteriosclerosis), the local vascular inflammations are replaced by numerous mild inflammations all over the blood vessels, where stimulation of platelets which leads to increase in platelet-poor plasma serotonin level does not occur, but whole blood serotonin level decreases due to serotonin consumption at so many inflamed regions.

These results indicate that early diabetic nephropathy can be detected by platelet-poor plasma serotonin level or the ratio of platelet-poor plasma serotonin to whole blood serotonin. Further, it is possible to know the exact pathologic condition of diabetic nephropathy by measuring platelet-poor plasma serotonin level or the ratio of platelet-poor plasma serotonin level to whole blood serotonin level, and whole blood serotonin level.

Though no significant difference was confirmed for platelet-poor plasma serotonin level or the ratio of platelet-poor plasma serotonin level to whole blood serotonin level by ANOVA statistic analyses, comparison of the respective groups by t-test revealed significant difference $P \leq 0.05$ between group 0 (healthy subjects) and group 1 (creatinine at most 1.2 mg/dl) in platelet-poor plasma serotonin level and between group 0 (healthy subjects) and groups 1, 2, 4 and 5 in the ratio of platelet-poor plasma serotonin level to whole blood serotonin level.

The present invention makes it possible to easily assess arteriosclerosis and diabetic nephropathy and is useful, especially in that it is possible to assess diabetic nephropathy and know its exact pathologic condition by measuring the serotonin levels both in whole blood, serum or platelet-rich plasma and in platelet-poor plasma. Further, it is useful also in that it is possible to assess diabetic nephropathy and know its exact pathologic condition from the ratio of platelet-poor plasma serotonin level to whole blood, serum or platelet-rich plasma serotonin level.

The entire disclosure of Japanese Patent Application No. 2005-062799 filed on Mar. 7, 2005 including specification, claims, drawings and summary is incorporated herein by reference in its entirety.

The invention claimed is:

1. A method for assessing diabetic nephropathy in diabetes patients having a creatinine level of at most 2.0 mg/dl comprising measuring the serotonin level in whole blood, serum or platelet-rich plasma and rating the serotonin level on such a scale that the lower it is, the more serious the diabetic nephropathy is.

2. The method according to claim 1, which comprises:
a) measuring the whole blood, serum or platelet-rich plasma serotonin level in an individual;
b) measuring the whole blood, serum or platelet-rich plasma serotonin level in a healthy individual; and
c) rating the whole blood, serum or platelet-rich plasma serotonin level obtained in a) on such a scale that the more it is below than the corresponding serotonin level in the healthy individual obtained in b), the more serious the diabetic nephropathy is.

\* \* \* \* \*